United States Patent
Wass et al.

(10) Patent No.: US 7,990,272 B2
(45) Date of Patent: Aug. 2, 2011

(54) RFID MEDICAL SUPPLIES CONSUMPTION MONITORING SYSTEM AND METHOD

(75) Inventors: John S. Wass, Concord, MA (US); J. Patrick Littlefield, Boxborough, MA (US); George Kocur, Cambridge, MA (US)

(73) Assignee: WaveMark, Inc., Littleton, MA (US)

( * ) Notice: Subject to any disclaimer, the term of this patent is extended or adjusted under 35 U.S.C. 154(b) by 0 days.

(21) Appl. No.: 12/616,630

(22) Filed: Nov. 11, 2009

(65) Prior Publication Data
US 2010/0141457 A1  Jun. 10, 2010

Related U.S. Application Data

(63) Continuation of application No. 11/383,422, filed on May 15, 2006, now Pat. No. 7,639,136.

(60) Provisional application No. 60/680,732, filed on May 13, 2005.

(51) Int. Cl.
G08B 13/14 (2006.01)
(52) U.S. Cl. .................................................. 340/572.1
(58) Field of Classification Search .... 340/572.1–572.9, 340/573.1; 705/3; 235/385
See application file for complete search history.

(56) References Cited

U.S. PATENT DOCUMENTS

| | | | |
|---|---|---|---|
| 7,132,945 B2 * | 11/2006 | Dunlap, Jr. | 340/572.1 |
| 7,183,921 B2 | 2/2007 | Bonnell et al. | |
| 7,286,900 B1 * | 10/2007 | Frederick et al. | 700/242 |
| 7,349,858 B1 * | 3/2008 | McGrady et al. | 705/3 |
| 2004/0008123 A1 * | 1/2004 | Carrender et al. | 340/825.49 |
| 2004/0031626 A1 * | 2/2004 | Morris et al. | 177/25.17 |
| 2004/0046020 A1 * | 3/2004 | Andreasson et al. | 235/385 |
| 2004/0144842 A1 | 7/2004 | Brignone et al. | |
| 2005/0149226 A1 | 7/2005 | Stevens et al. | |
| 2005/0149379 A1 | 7/2005 | Cyr et al. | |
| 2005/0200453 A1 | 9/2005 | Turner et al. | |
| 2005/0201450 A1 | 9/2005 | Volpi et al. | |
| 2005/0280536 A1 | 12/2005 | Hamilton et al. | |
| 2006/0082440 A1 | 4/2006 | Glaser et al. | |
| 2006/0089918 A1 | 4/2006 | Avanzi et al. | |
| 2006/0136167 A1 * | 6/2006 | Nye | 702/127 |

\* cited by examiner

*Primary Examiner* — Phung Nguyen
(74) *Attorney, Agent, or Firm* — Houston Eliseeva LLP

(57) ABSTRACT

A system and method for tracking supplies, particularly medical supplies, and specifically individual medical items, to the end of the product lifecycle to the point of utilizes. RFID tag technology is utilized. This has the advantage of enabling a system that requires less or no active intervention by the medical services delivery staff, such as nurses and doctors. Nonetheless, the system is applicable to other stand-off identification systems including taggant-based systems. The system provides for the monitoring of items, such as medical items, between the distribution center, facility stock rooms and inventory cabinets, and the procedure rooms in which the items are put into use. In one example, system and method associate stand-off, such as RFID, readers with waste-disposal or refuse containers and/or readers located near the point of usage, such as in or associated with the procedure rooms in order to monitor the endpoint of the product lifecycle. Thus, the knowledge of medical item disposal or disposal of the medical item's packaging is combined with one or more prior detections of the medical item, e.g., at acquisition and when moved to a different location such as storage, to generate a usage history for the item. In all or more cases, this knowledge is acquired with out human intervention by judicious location of readers at the distribution center and/or medical facility.

6 Claims, 8 Drawing Sheets

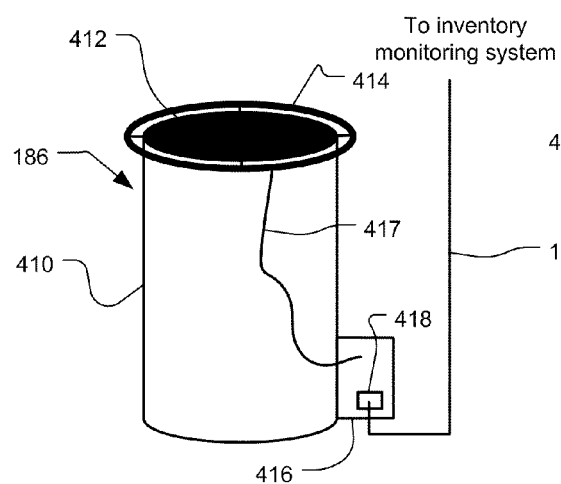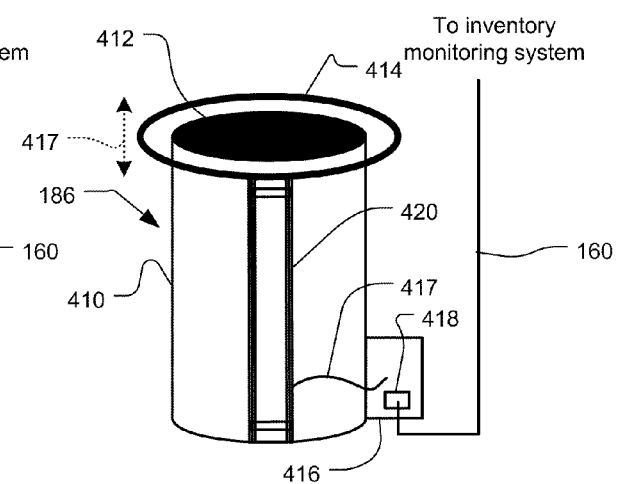
Fig. 5A    Fig. 5B
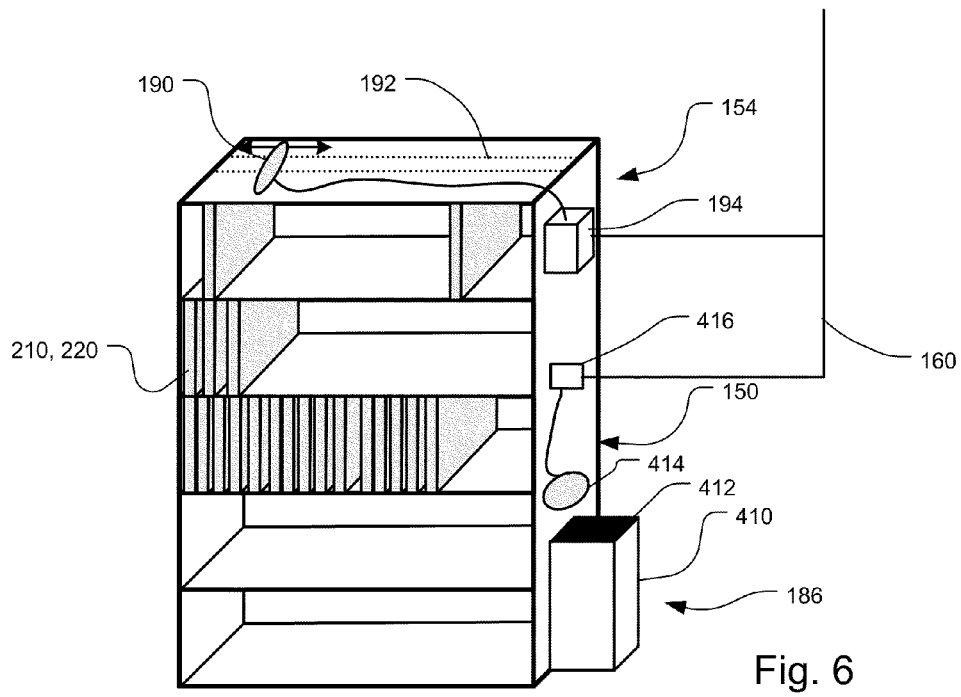
Fig. 6

RFID MEDICAL SUPPLIES CONSUMPTION MONITORING SYSTEM AND METHOD

RELATED APPLICATIONS

This application is a Continuation of U.S. application Ser. No. 11/383,422, filed on May 15, 2006, which claims the benefit under 35 USC 119(e) of U.S. Provisional application No. 60/680,732, filed May 13, 2005, both of which are incorporated herein by reference in their entirety.

BACKGROUND OF THE INVENTION

Radio Frequency Identification (RFID) systems have been proposed for the tracking of medical supplies in hospitals. Such systems typically involve one or more readers and many tags, each of which is attached to an item being monitored. In the case of medicaments, single-use medical devices, and implantable medical devices, RFID tags are typically affixed to or made part of the medicament container, e.g. medicine bottle, or medical device container, e.g., disposable packaging for the stent or orthopedic implant.

RFID tags take the form of integrated circuits, with associated antennas, that encode a unique serial number. The reader is generally in a fixed location, and items with RFID tags are detected when they enter or leave the electromagnetic field of the reader. For example, RFID readers are often placed at multiple distributed locations associated with an item's supply chain in order to monitor the item as it passes through manufacturing, transportation, and distribution. Each reader captures the RFID tag serial numbers of each item as it enters the reader's interrogation field, and data collected from all readers facilitate item tracking over time, through the chain.

Tracking using these systems generally deteriorates as the items being tracked approach the time and place of use, e.g., consumption, implantation, exhaustion, or disposal. It is therefore difficult to trace a particular item's full history.

For example, the most common practice in accounting for product use and disposition is based on manual data entry, sometimes assisted by bar-code scans. These manual procedures record the usage and disposition of supplies. Moreover, data entry often must be performed under time constraints that do not allow verification of the data entered. Consequently, error rates can be high and data quality is often poor. Indeed, the personnel performing these procedures often do not recognize them as high-priority tasks.

SUMMARY OF THE INVENTION

The present invention concerns a system and method for tracking supplies, particularly medical supplies, and specifically individual medical items, to the end of the product lifecycle to the point of use. In the preferred embodiment, RFID tag technology is utilized, since it has the advantage of enabling a system that requires less or no active intervention by medical services delivery staff, such as nurses, medical administration personnel, or doctors. Nonetheless, the system is applicable to other stand-off identification systems including taggant-based systems, such as Raman taggants systems. The system provides for the monitoring of items, such as medical items, between the distribution center, facility stock rooms and inventory cabinets, and the procedure rooms where the items are put into use.

In one example, system and method associate stand-off, such as RFID, readers with waste-disposal or refuse containers and/or readers located near the point of usage, such as in or associated with the procedure rooms in order to monitor the endpoint of the product lifecycle. Thus, the knowledge of medical item disposal or disposal of the medical item's packaging is combined with one or more prior detections of the medical item, e.g., at acquisition or when moved to a different location such as storage, to generate a usage history for the item. In all or more cases, this knowledge is acquired without human intervention by judicious location of readers at the distribution center and/or medical facility.

The system and method further utilize an inventory management system for receiving, from the RFID readers, for example, sensed tag information associated with the items. A database associates the items with the tag information and with the stand-off readers with their physical locations, and the items with a location and time when sensed by a reader. An inference module generates usage histories for the items based on data collected in the database.

In medical and other applications, the readers are configured to detect the presence of tags entering or residing in waste-disposal receptacles. This feature allows data to be developed about the status, location, time, and other characteristics marking the end of the item's useful life or its consumption, e.g., in the course of a medical procedure. These characteristics include the procedure associated with the final use of the product, corresponding billing data, inventory-control data, personnel involved in the procedure, and other tagged items used in the procedure. Reading the product tag at the time of disposal provides accurate confirmation that the product was in fact used at the date, time, and location at which the RFID tag was detected in the refuse container and recorded. RFID tags and readers therefore can be used to determine the final disposition of an item without the need for manual (and potentially unreliable) data entry activity by the personnel associated with the procedure.

In general according to one aspect, the invention features a medical item tracking system for medical items at a medical facility. The items have associated radio frequency identification (RFID) tags. The system comprises a medical supply location having a supply location reader for reading RFID tags of the medical items stored in the supply location and a procedure room RFID reader in or near a procedure room in which the medical items are used on patients of the medical facility. The procedure room RFID reader reads the RFID tags of medical items removed from the medical supply location for use in the procedure room.

In the preferred embodiment, the RFID tags are affixed to packaging for the medical items or incorporated into packaging for the medical items. The supply location reader automatically reads the RFID tags contained in the supply location. The procedure room RFID reader in one example is associated with a refuse container associated with the procedure room.

A management system is used to receive RFID tag information from the supply location reader and the procedure room RFID reader and track movement of medical items between the medical supply location and the procedure room. This management system classifies medical items as used at the medical facility if the RFID tags of the medical items are read in the medical supply location and then read by the procedure room RFID reader.

In general according to another aspect, the invention features a medical item tracking system for a distribution center. The medical items have associated radio frequency identification (RFID) tags. The system comprising supply location having a RFID supply location reader for reading RFID tags of the medical items stored in the supply location; and a refuse reader in the distribution center for reading the RFID tags of medical items placed in a refuse container.

In general according to another aspect, the invention features a medical item tracking method for medical items at a medical facility having associated radio frequency identification (RFID) tags. The method comprises reading RFID tags of medical items stored in a supply location, indicating medical items as being in an inventory when the RFID tags of the medical items are read at the supply location, reading RFID tags in or near a procedure room, and indicating medical items as being used when the RFID tags of the medical items are read in or near the procedure room.

In general, according to still another aspect, the invention features a method for tracking medical items in a supply chain at a distribution center. This method comprises detecting medical items in storage locations at the distribution center and reporting removal of the medical items from the storage when the medical items are no longer detected in the storage locations. An inventory database system changes the status of the medical items to removed from the storage locations in response to receiving a removal report.

In a preferred embodiment, the step of detecting the medical items in the storage locations comprises incorporating standoff readers in the storage cabinets. One example of a standoff reader is a radio frequency identification (RFID) reader. Standoff tags are associated with the medical items. The presence of the medical items is then detected by determining whether the standoff tags are within a detection field of the storage cabinets. The step of reporting removal of the medical items from the storage locations is performed if the standoff tags of the medical items are removed from the detection field.

In a preferred embodiment, the disposal of the medical items is also detected. A disposal report of the medical items is then provided to the inventory data base system, which changes the status of the medical items to indicate this disposal. In one example, the step of detecting disposal of medical items comprises associating RFID readers with a refuse container at the distribution center and then detecting the presence of the medical items within a detection field of the readers as an indication of the disposal.

Also, the status of the medical items relative to the distribution center is modified if the presence of the medical items is detected at a hospital. Specifically, the presence of the medical items is reported to the inventory database system, which changes the status of the medical items to indicate this presence.

In a preferred embodiment, the step of detecting the presence of the medical items at the hospital comprises incorporating RFID readers in storage cabinets at the hospital and associating RFID tags with medical items and then detecting the presence of the medical items within the detection field of the storage cabinets.

In general, according to another aspect, the invention features a method for tracking medical items in a hospital. This method comprises detecting medical items in storage locations at the hospital and reporting removal of medical items from the storage locations when the medical items are no longer detected in the storage locations. An inventory database system then changes the status of the medical items to indicate removal in response to receiving this removal report.

In a preferred embodiment, usage at that hospital is also detected such a by associating RFID readers, or other standoff readers, with refuse containers or procedure rooms where the medical items are used in the course of medical treatment.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIGS. 5A and 5B are schematic perspective views of two embodiments of an RFID refuse container system according to the present invention;

FIG. 6 is a schematic perspective views of an RFID refuse container system associated with a RFID cabinet according to the present invention;

DETAILED DESCRIPTION OF THE PREFERRED EMBODIMENTS

Hospital Tracking System

Figure 1:
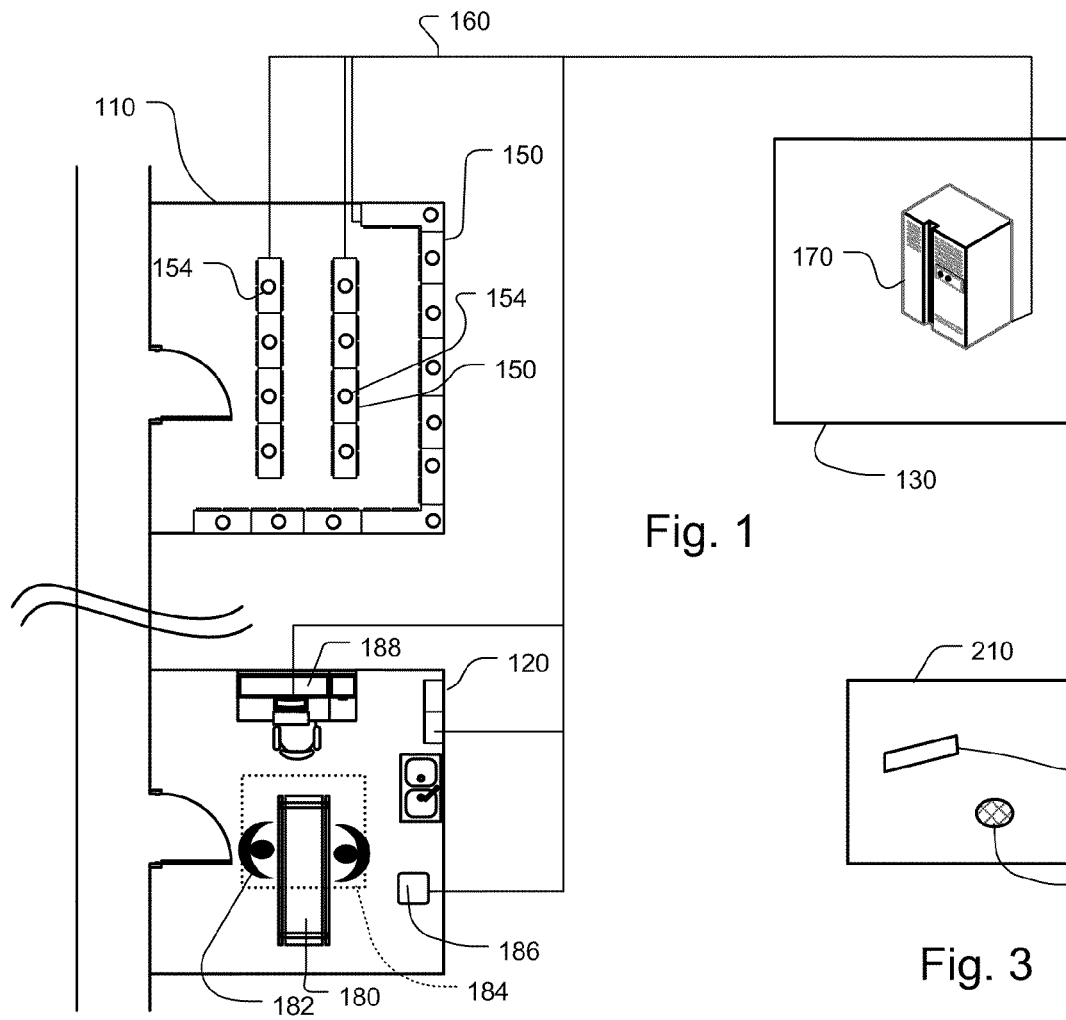
FIG. 1 is a schematic diagram illustrating a medical item tracking system according to an embodiment of the present invention.

FIG. 1 shows one embodiment of a tracking system which has been constructed according to the principals of the present invention.

The tracking system is described in the context of a hospital or other medical care delivery facility such as a long-term care facility, doctors' office, animal hospital, and other institution that delivers medical care including state institutions and prisons.

The hospital or other medical care facility generally comprises a medical supply room 110 that is devoted to housing supplies including medical items, a procedure room 120 where the medical items are used, such as consumed or implanted in patients, and a local or off-site server or network area 130 that houses the information technology infrastructure for the facility.

In more detail, the medical supply room 110 in the example comprises a number of medical supply cabinets or other storage units 150. In the preferred embodiment, each of the medical supply cabinets 150 is a radio frequency identification (RFID) cabinet that includes an associated RFID reader 154. These medical supply room/cabinet readers 154 are capable of detecting and reading RFID tags of medical items stored in the cabinets 150.

Figure 2:
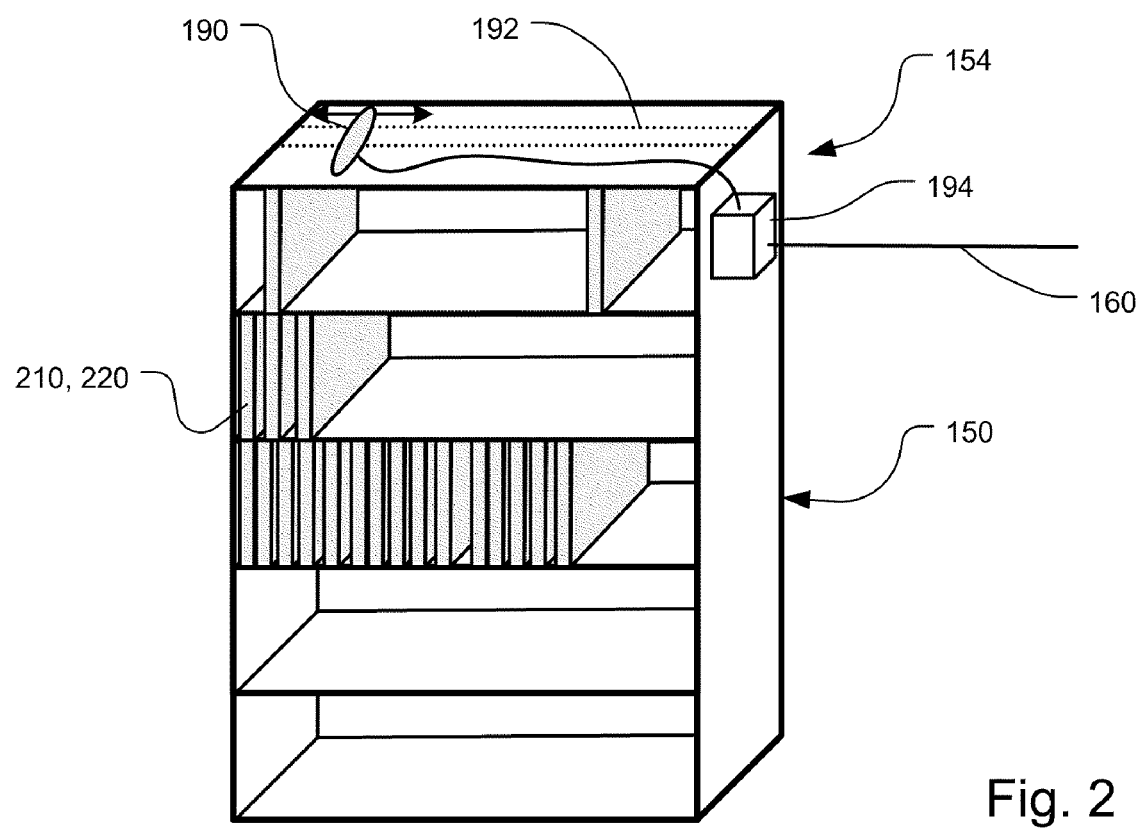
FIG. 2 is a schematic perspective view of an RFID cabinet used in the inventive system.

FIG. 2 shows one example of an RFID cabinet 150. The RFID readers 154 for the medical cabinets 150 comprise antennas 190 that are moved in the cabinets to enable the RFID readers to scan for RFID tags in the storage cabinets 150. This antenna scanning facilitates detection of the tags regardless of orientation within the cabinets or proximity to other RFID tags.

Specifically, in the example, the cabinet 150 comprises medical items 220 stored in item packages 210. In a specific example, they are stored on various shelves. The cabinet 150 interrogates the various RFID tags of the items 210 using one or more cabinet antennas 190. Here, antenna 190 of the cabinet reader system 154 is scanned along the length of the cabinet on an antenna conveyor 192. The RFID controller 194 for the cabinet 150 uses the information from the antenna to read the RFID tags of the items contained in the cabinet 150. The information is transmitted via a network interface on the controller 194.

Returning to FIG. 1, the RFID cabinet readers 154 of the medical supply location 110 are networked on to a communications network 160. Specifically, the readers 154 communicate via the communications network, such as a local area network (LAN), to an inventory management system 170. In this way, the inventory management system 170 is able to track the presence of the medical items in the storage cabinets 150 in real-time without intervention by staff. Thus, there is no action required by the hospital personnel in order to enable the inventory management system 172 to detect the presence of the medical items. Further, there is no staff intervention required when items are removed since the periodic scan of the cabinet contents by the readers 154 detect removal, which is then reported to the inventory management system 170.

Most often the medical items 220 are removed from the medical supply location 110 when they are going to be used in the treatment of patients at the facility. Medical procedures requiring the items often are performed in procedure rooms 120. In some examples, this room is simply a patient examining room for simple procedures such as injections. In other examples, the procedure room is an operating room a diagnostic or monitoring room, or a single use room such as a catheter lab.

In one example, the procedure room 120 comprises, for instance, a procedure table 180 for the patient. The medical personnel 182 will then perform the procedure on the patient. Typically, there is a sterile field 184 that is defined in which the sterile items of the operation are contained.

The procedure room 120 has one or more associated procedure room RFID readers. In the illustrated example, the procedure room has an RFID reader associated with a refuse container 186 system and/or an RFID reader associated with a workstation 188. These RFID readers are used to detect the usage of the medical items in the context of the procedure taking place in the procedure room 120.

In other embodiments, the procedure room RFID readers are located in an adjacent room such as a preparatory room. Alternatively, the RFID readers are located at the entrance to the procedure room so that RFID tags of items are read when they are carried into the room.

In one example, the medical personnel 182, after removing the medical item from its container dispose of the container in the refuse container system 186. In this example, the RFID reader of the refuse container 186 automatically detects the presence of the RFID tag in or on the medical item packaging. This information is sent via the communications network 160 to the inventory management system 170.

In an alternative example, the RFID reader associated with the workstation 188 is used to detect the usage of the medical item. Specifically, in this example, the hospital inventory management protocol requires the hospital personnel scan the RFID tag of the medical item at the RFID reader of the workstation 188 before, during, or after the procedure. This requires more manual intervention by the personnel 182.

In many aspects of the present system usage medical items is inferred from the detection of the RFID tag of the medical item by an RFID reader associated with the procedure room, such as the RFID reader integrated with the refuse container system 186 or the workstation 188. The scan at the time and place of usage provides strong evidence of the item end of life thereby improving the quality of the information contained in the inventory system 170.

Figure 3:
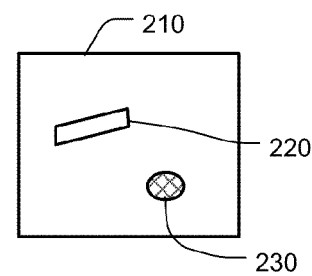
FIG. 3 is a schematic plan view of a medical item with RFID tracking.

FIG. 3 illustrates one way of associating the RFID tags with a medical item. Specifically, a package 210 is provided that contains the medical item 220, typically in a sealed sterile environment. The RFID tag 230 associated with the medical item 220 is attached, fixed or made part of the outside of the packaging 210. In this way, by tracking the RFID tag 230, the medical item package 210, and therefore the medical item 220 is tracked in the hospital or distribution center. In other examples, the RFID tag is incorporated into the medical item itself.

Figure 4:
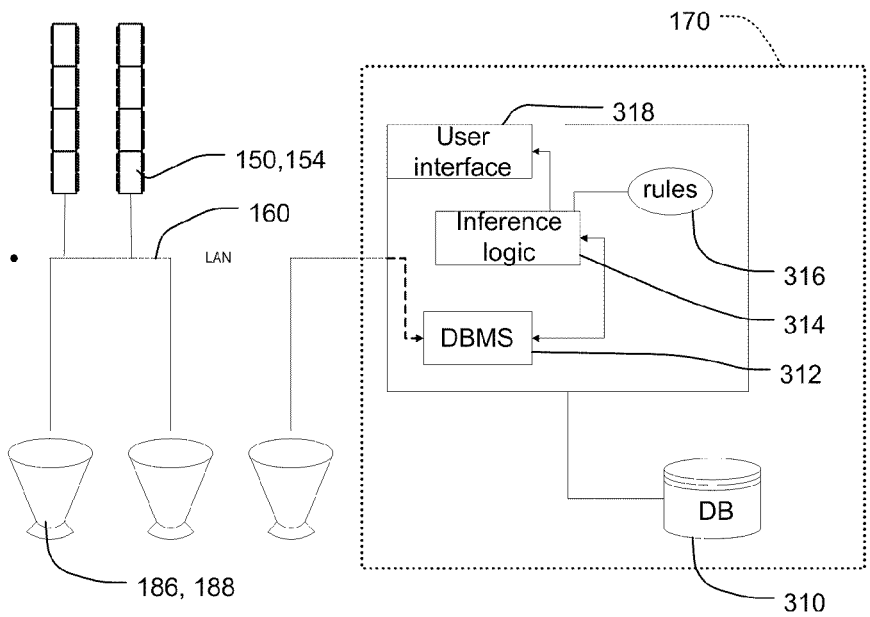
FIG. 4 is a schematic diagram illustrating a network for the medical item tracking system according to an embodiment of the present invention.

FIG. 4 illustrates the relationship between the communications network 160, the inventory management system 170, and the remotely placed RFID readers 154 of the medical supply cabinets 150 and the procedure room RFID readers associated, for instance, with the refuse container systems 186 and workstations 188.

In more detail, as discussed, the medical cabinets 150 have RFID readers 154 that are networked on to the communications network 160. Similarly, the refuse containers 186/workstations 188 for various procedure rooms in the hospital are similarly linked via the local area network 160. This connectivity allows these devices to transmit information concerning the scanned RFID tags of medical items, which are detected in the medical supply cabinets 150 or the refuse containers 186, to the inventory management system 170.

Depending on the implementation, the communications network 160 is either a wired network, a wireless network, or a hybrid network. For example, the RFID reader of relatively stationary objects, such as cabinets, will typically connect through wired connections. In contrast, the readers of less stationary objects, such a refuse container, will sometimes connect through wireless or powerline data connections.

The inventory management system comprises a database 310. This stores the inventory information. The database is managed by a database management system (DBMS) 312 that updates the information in the database 310. This database management system 312 uses inference logic 314 and a set of rules 316 to infer the status of medical items based on the information from the RFID readers 154 of the cabinets 150 and from the refuse containers 186. This information is then presented to users via a user interface 318. Also, the user interface can be used to obtain manually entered information concerning the status of medical items in the hospital.

Ideally, the identity or category of an item, along with its RFID identifier, are entered into database 310 when the item physically enters the facility. Each time a reader senses the item's RFID tag, the associated location, time and any status information that are unambiguously derived from the reader (e.g., if the reader is associated with a trash receptacle, sensed items are usually marked as discarded) are entered into the database record for that RFID identifier.

For example, an RFID trash reader, after reading a tag, transmits the serial number through the communications network 160 to the DBMS 312 of the inventory management system 170. The DBMS associates the RFID tags, read as items or discarded packagings, with earlier readings for the same item (generally involving different readers, not necessarily associated with refuse containers, such as those in cabinet 150.). The inventory management system determines, based on the times and locations of all RFID tag read events associated with the items, the disposition, inventory status, billing data, personnel involved in the procedure at the point where the trash was generated, and other information associated with the items.

The user interface 318 allows users to obtain the raw record data for a selected identifier. However, the inference module 314 is used to analyze the entries in a record according to predefined rules 316, and, based on those rules, to infer one or more aspects pertaining to the movement and usage of the item associated with the identifier. The inferred information is entered into the database record associated with the item's RFID identifier, and viewed by users via the user interface. The rules also determine when entries are flagged and dictate appropriate actions when discrepancies or error conditions are discovered.

FIGS. 5A and 5B illustrate two implementations of the refuse container system 186 with integrated RFID readers.

Generally, the RFID reader of the refuse container 186 is used to detect all of the tags within an electromagnetic field that encompasses the entire waste container or reads the tags as they pass into the container. The reader includes a controller that decodes the unique serial number of each sensed RFID tag.

Specifically, FIG. 5A illustrates an RFID reader with a stationary antenna. Specifically, the refuse container system 186 comprises a container 410. This is a typical, common trash container configuration that combines basically a fluid tight body having an opening 412 into which the refuse is inserted into the container 410.

In this embodiment, an RFID reader antenna 414 is located near the opening 412. In one example, it is located at the level of the opening. In other examples, it is located above the opening 412. As a result, medical item packages 210 pass through the opening 412 and the electromagnetic read field created by the RFID reader antenna 414. This allows the detection of the RFID tags 220.

An RFID reader controller 416 drives the antenna 414 via a RF umbilical 417 and interprets the information from the antenna to determine the serial number and associated data encoded in the RFID tag. This tag information is transmitted out onto the communications network 160 via a network interface 418. In a typical example, this network interface is an Ethernet connection or wireless link.

FIG. 5B shows an alternative embodiment comprising a scanning RFID antenna 414. In this example, the RFID antenna 414 is transported by an antenna conveyor 420. This conveyor 420 moves the RFID antenna 414 vertically, over the length of the refuse container 410, allowing the RFID antenna 414 to detect the RFID tags of medical item packages contained within the container 410 of the refuse container system 486. In one example, the conveyor 420 is a stepper motor/lead screw system, enabling the antenna to sweep the container 410 from its top to bottom.

The antenna 414 is connected by a flexible RF (radio frequency) umbilical cable to the RFID reader controller 416 in the base of the unit. The RFID reader controller is usually implemented as a single board computer controller. The single board computer has an operating system and software that controls the conveyor 420, obtains the tags read from the RFID tags, eliminates duplicate reads and sends the tag information, along with a time/date stamp of the read time, to the inventory management system 170. In this way, the contents of refuse container system 186 are actively interrogated, and the RFID tags are detected and read despite their position and location.

In other examples, fixed loop antennas at the top, middle and/or bottom of the trash receptacle, encircling or nearly encircling the receptacle, are used. As the trash container fills, the ability of the bottom and then the middle antennas to read product tags declines, but they are still within the read range of all or most item tags in the receptacle. If the item tag is in an orientation that can be read by a fixed antenna, the bottom and middle antennas will read it with high likelihood when it is in motion, and with good likelihood when it is stationary. As additional trash is placed in the receptacle, existing trash is often displaced, providing an additional opportunity for its tags to be read by the fixed antennas.

A rotating field for either or both of the previous approaches will also increase the probability of read accuracy for random orientation tags as they enter the trash reader.

The antenna and associated design elements of the receptacle address difficulties of the environment as follows:

1. Difficult tag orientations. The moving antenna or rotating fields will see each tag in the trash in many orientations in three dimensions, and will be able to read virtually all tags. The fixed antennas will see most tags during most reads. The top antenna will read most tags upon entrance to the trash, since the tags will be moving at an appropriate velocity to be read. As the trash resides in the receptacle, it will often be moved when additional trash is placed in the receptacle. Both the motion and the change in orientation will allow almost all tags in the trash to be read by the stationary antennas.

2. Tags separated from packaging. This poses no problems. The tags can be read even if separated from packaging. The database management system contains data to associate every tag with the product item to which it was attached. The tags must maintain physical integrity, which is assured in almost all cases. In some example, two tags are placed on each product, so that if one tag is damaged or in a position that cannot be read, the trash reader will still read the other. This is a major advantage over bar codes, which can be easily damaged in a trash receptacle to the point of unreadability.

3. If tags are closely adjacent to each other, they are difficult to read. As trash shifts, the moving antennas will be able to read tags that may not have been read earlier, after even small displacements. Fixed antennas will pick up tags as they are thrown in the trash and will also read them as the trash receptacle is removed from the housing containing the antennas, providing a second opportunity to read the tags in the trash.

4. RFID tags generally withstand wetness and other conditions that affect the ability to read bar codes. The RFID trash reader are able to read all or most tags in typical disposal environments in medical and distribution center settings, where large quantities of liquid will not be present in the trash.

The trash reader has a power supply, either battery or wired, to power the RFID reader, its associated antenna, the digital processor and local area network (LAN) connection. The trash reader desirably withstands liquids, corrosives, medical wastes and other conditions typical of trash disposal. It is preferably washable, capable of withstanding sterilization through chemical methods, durable enough to withstand typical usage of trash receptacles, portable, relatively lightweight, and of appropriate size for the process and location.

Distribution Center Tracking System

The previous discussion has focused on techniques and devices appropriate for stand-off tracking of items, such as medical items, at the point of use, such as a medical facility. In many cases, tracking is initiated, especially for high value items such as those associated with medical applications, at the point of manufacture, followed through to a distribution center and then to the facility. Principles of the present invention can be extended to these other locations.

FIG. 6 illustrates another example of an RFID refuse container system. This embodiment is relevant both in the hospital context but also in the context of a distribution center or manufacturing location.

In this example, the refuse container system 186 is associated with the RFID supply cabinet 150. Specifically, the cabinet 150 has shelves for holding medical items 220 stored in item packages 210. The cabinet 150 interrogates the various RFID tags of the items 210 using cabinet antenna 190, which is scanned along the length of the cabinet on the antenna conveyor 192. The RFID controller for the cabinet 114 uses the information from the antenna to determine the contents of the RFID tags contained on the shelves 510 of the cabinet 150.

An RFID refuse container system 186 has the container 410 and has an RFID antenna 414 located above the container mouth 412. Thus, in this example, as the medical items are disposed of, such as after they have expired or exceeded their useful life, their disposal in the refuse container system 186 is recorded and transmitted over the communications network 160 using refuse container controller 416.

In this example, the trash reader detection circuitry is external and associated with another device or object, the storage cabinet, in proximity to the trash receptacle container 410. The antenna is located on the exterior of the cabinet (or other device) at a height and orientation consistent with placement of a waste receptacle adjacent to or below the antenna, so that the antenna—although not physically mounted on the trash receptacle—nonetheless reads all RFID tags that are placed in the container. In this example, the cabinet or other device may be marked to indicate the position at which the waste receptacle should be placed.

Also, in one implementation, the waste container itself has one or more RFID tags placed in or on it, thereby allowing the reader circuitry 416 to detect its presence and to identify the receptacle uniquely. In this way, a single reader is able to cover multiple trash receptacles, each identified uniquely by virtue of RFID tags associated therewith.

Moreover, associating an RFID reader with a storage cabinet allows withdrawal events to be recorded. When an item previously sensed is removed from the cabinet's detection field, the item's removal is reported as an event to the inventory management system. This adds to the information associated with the item and assists with inferences as to the item's state. Additional RFID readers are preferably placed in other locations, e.g., hallways and doorways. Again, the more times an item is sensed, the greater will be the detail with which its history may be traced, and the less inference that will be necessary to complete that history.

During setup, the RFID circuitry prompts responsible personnel to place a waste receptacle container 410 in the appropriate position if one is not present. In this system embodiment, the waste receptacle does not require its own reader, power, digital processor or LAN connection. When the external reader detects an item that is being discarded, it reports to the DBMS 312 the RFID identifier associated with the item as well as the trash receptacle(s) within its reading range. In instances where an item has two or more tags, the inventory management system associates location and time information with records corresponding to each tag ID. In particular, the DBMS (and, in some implementations, the trash reader as well) records the RFID tag serial number, data and time of the reading, and waste receptacle unique identifier, and records a disposal event. If the RFID reader is on a cabinet, a unique identifier associated with the cabinet is recorded as well.

A system described above provides a complete record of product usage and disposition for all products used at a facility or in a distribution center. Items not recorded by a trash reader are usually still in inventory, or must leave the facility through other controlled means such as manufacturer recalls, returns, expiration returns, defective returns, patient implants, or other related processes. The trash reader provides accountability at the end of a product life cycle in a manner similar to the way manufacturing controls document the start of a product life cycle.

State-Based Medical Item Tracking

Figure 7:
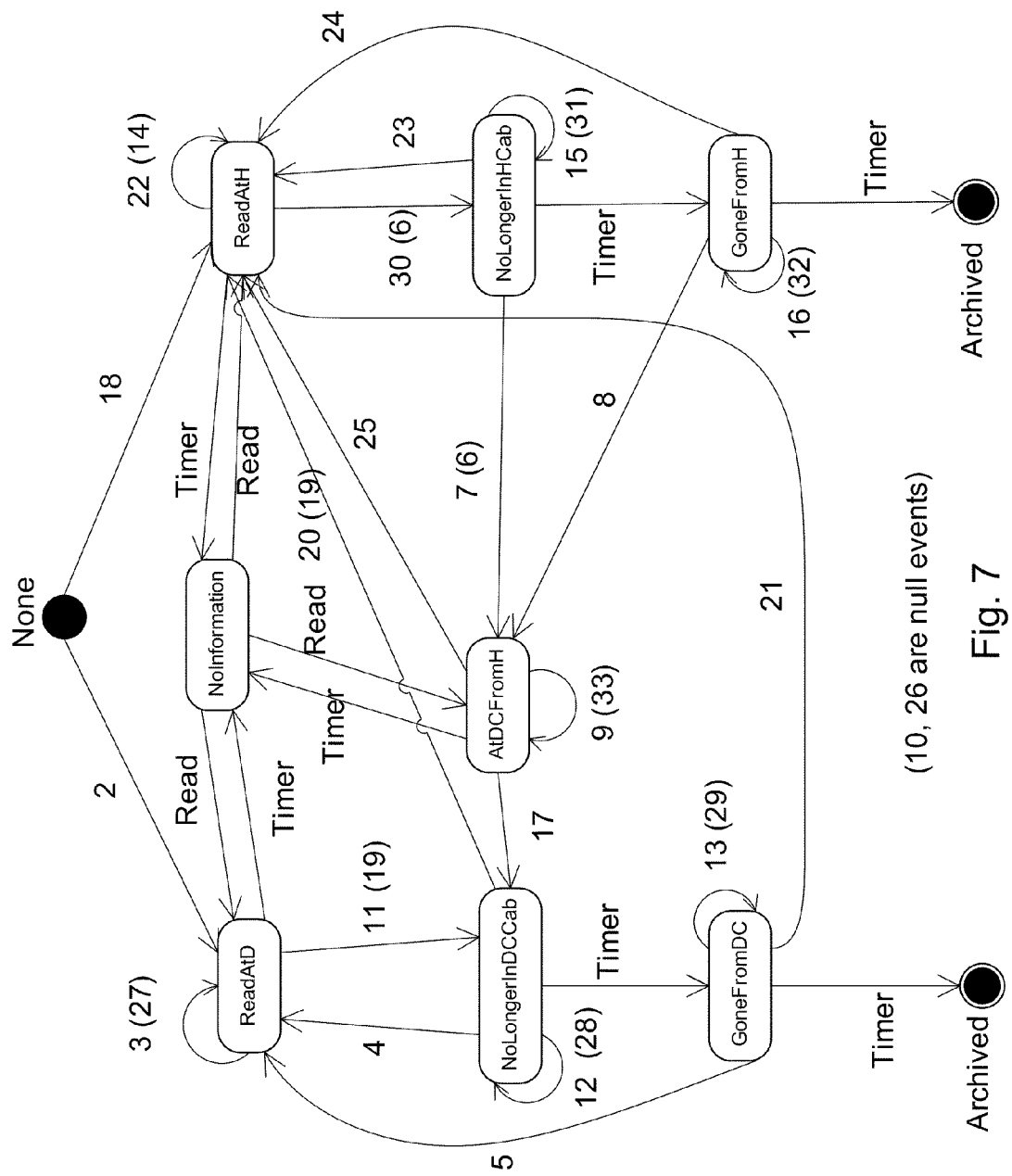
FIG. 7 through 9 are state diagrams showing a finite state machine that is used to determine the status of medical item usage in the supply chain.
Figure 8:
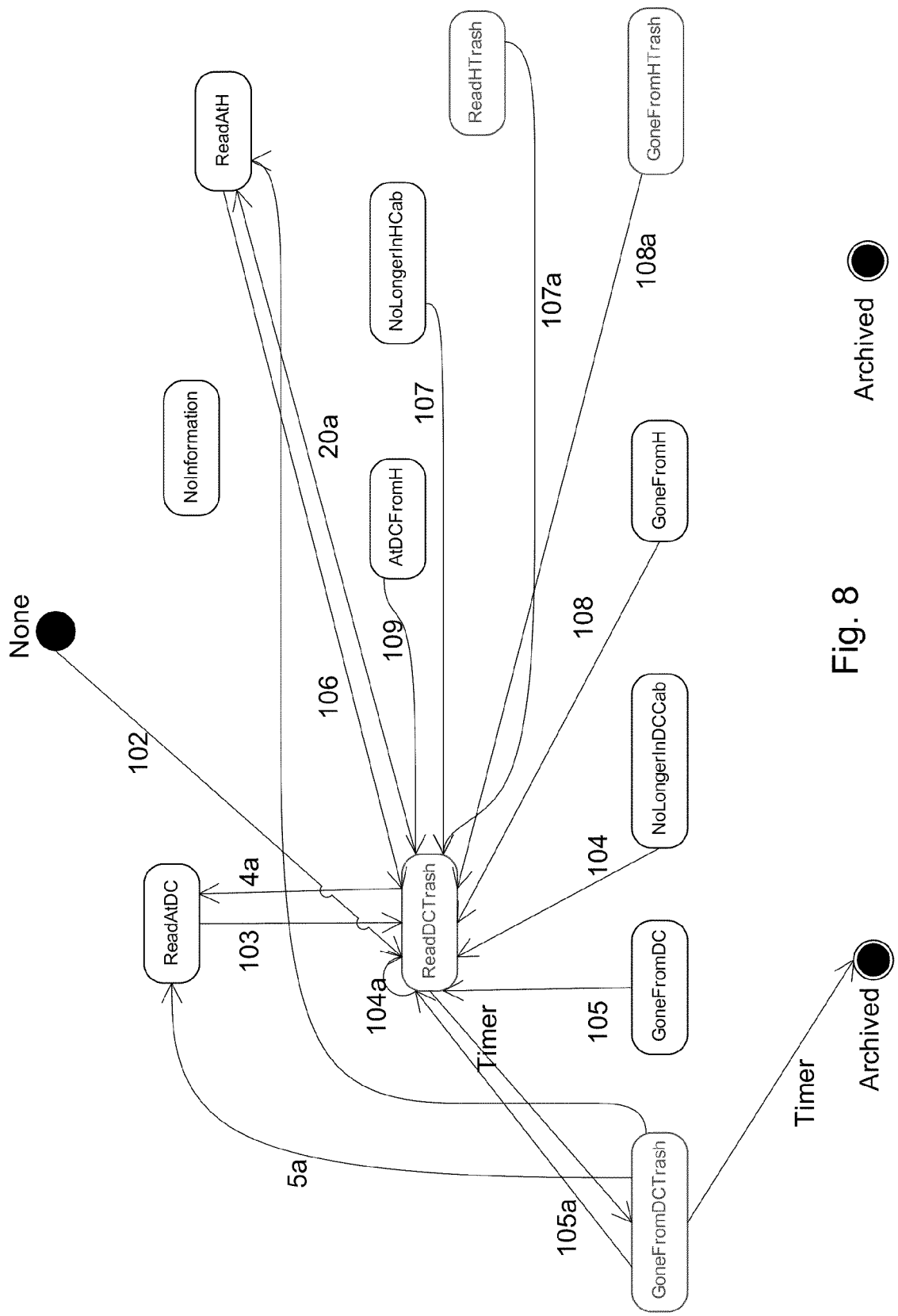
Figure 9:
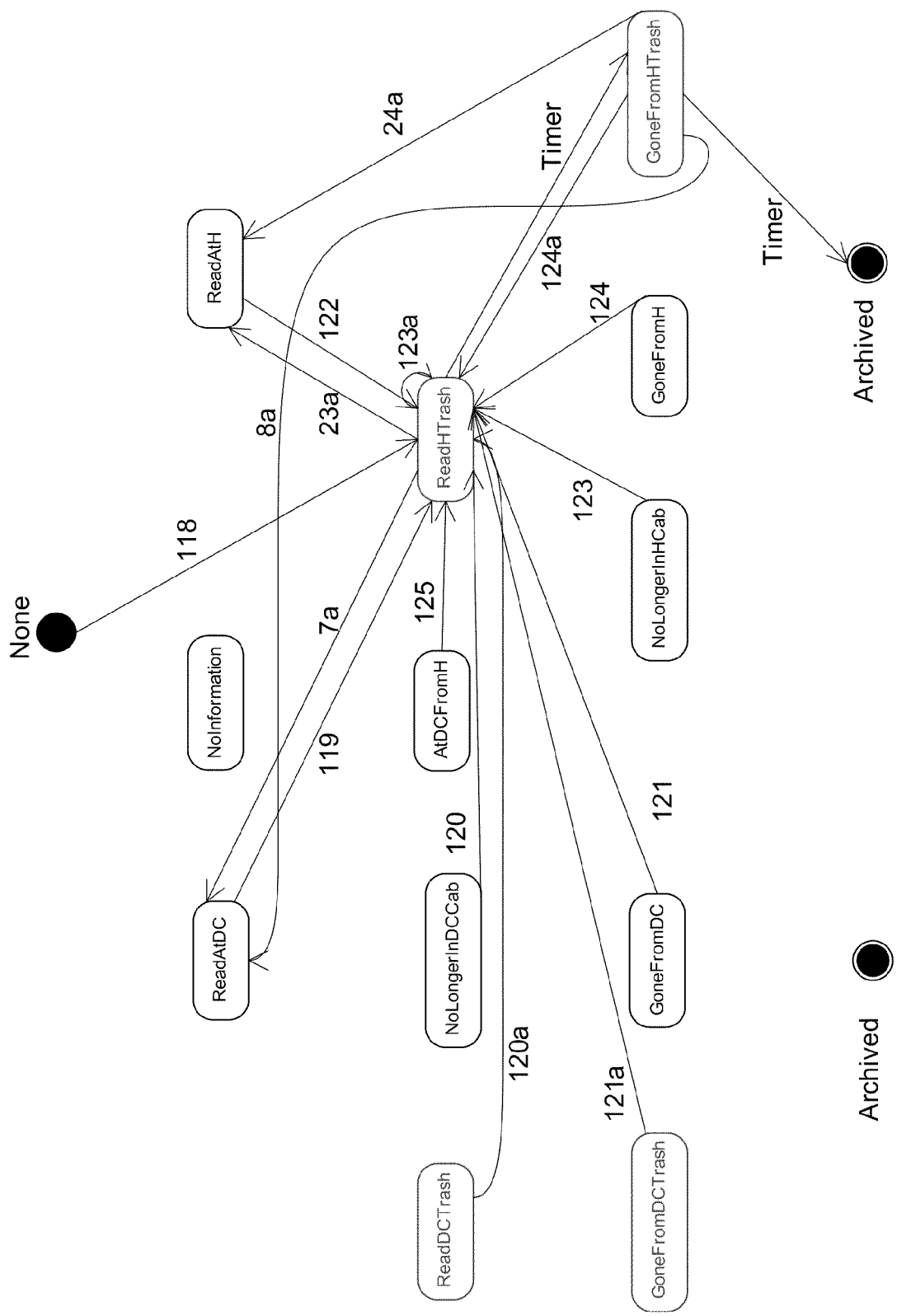

FIGS. 7 through 9 show a finite state machine that is implemented to use the trash reader output along with data collected RFID cabinets and other sources to determine the status of medical item usage in the supply chain.

In the figures, D or DC is used for the manufacturer distribution center, H or Hosp for the hospital department, Cab for the RFID cabinet 150, and Trash for the RFID trash or refuse reader 186. Both DC and H have RFID readers for stock being shipped and received, and either or both preferably further have trash or refuse readers.

The figures show product states and their transitions, called dispositions. The numbers in FIGS. 7 through 9 are keyed to the row numbers in tables 3 and 4 below that describe the state transitions. All of these states and transitions are inferred from the RFID readers at the DC and H, for both shipped/received stock and for trash readers at both locations.

FIG. 7 shows the basic transitions between H and DC. FIG. 8 adds the states and transitions associated with the hospital trash reader. FIG. 9 adds the states and transitions associated with the DC trash reader. Most of these transitions, while possible, are highly unlikely and represent errors. All are included in the finite state machine for completeness and to support error detection.

In one implementation, the database management system 312 of FIG. 3 writes the current state, current disposition, next state, next disposition, first RFID read date and time, last RFID read date and time, RFID read location, type of location (hospital, DC, other supply chain point) and supporting data to the database 310 based on the inference logic 314 and rules 316. Users access the database with preferably a Web application that supports the system via interface 318. The application processes the data from the finite state machine and database 310 to produce measures of transactions and inventory levels at cabinets and other points with RFID readers. The trash readers at the DCs and hospitals enhance the accuracy necessary for system reports.

A brief summary of the finite state machines of FIGS. 7-9 is given below. The set of states and dispositions below account for the large majority of actual transactions. Many of the dispositions and states in the figure above are error conditions and should occur rarely. In the figures:

1. The black dot at the top is the start.
2. A medical items will be first read either at DC or H, not both.
3. If the medical item's first read is at the DC, the normal case, it will either stay there indefinitely (until it expires in the worst case), or it will be read in the trash reader at the DC, or it will leave.
4. If the medical item leaves the DC, it is either read at a hospital within a given time period (typically 1-2 days) or it is lost in transit or may be at a manufacturer sales representative, who may not have an RFID reader. It may be read in the DC trash, which indicates it has been disposed.
5. If the medical item is first read at H, it will either stay there indefinitely (until it expires, in the worst case), or it will be read in the trash reader, or it will leave.

6. If the medical item leaves H, it is either read at the DC within some period (if returned) or after some period (typically two weeks) it will be assumed not to be read again.

7. The medical item may also be read again at H, which will occur if it was taken from a cabinet and then returned to the cabinet.

The possible states in the system, as shown in FIGS. 7-9 are:

TABLE 1

| System states |
|---|
| <none> |
| ReadAtDC |
| NoLongerInDCCab |
| ReadDCTrash |
| GoneFromDC |
| GoneFromDCTrash |
| ReadAtH |
| NoLongerInHCab |
| ReadHTrash |
| GoneFromH |
| GoneFromHTrash |
| AtDCFromH |
| NoInformation |
| UnableToLocate |

When the system detects a state change for a medical item from RFID reads, or if a user enters a manual disposition, the DBMS 312 writes its state transition or disposition into the database 310. The disposition (state change) occurs automatically when a box leaves a DC or H, arrives at a DC or H, is read in the trash, or is not seen for a time period. Manual dispositions (Manual) along with dispositions from information from RFID readers (RFID) and dispositions associated with timers, i.e., an item has spent too much time in a state, (Timer) are described below.

The list of valid disposition codes is:

TABLE 2

| System dispositions, or state transitions | | |
|---|---|---|
| Disposition codes: | Type | DispositionGroup |
| Defective | Manual | Unresolved |
| ErrorAtDCAfterGone | RFID | Unresolved |
| ErrorAtHospAfterGone | RFID | Unresolved |
| ErrorRecdAtHosp | RFID | Received |
| ExpiredInHosp | Timer | Unresolved |
| InHospital | RFID | Received |
| InTransitToDC | Manual | Returned |
| InTransitToHosp | Manual | InTransit |
| InTransitToRep | Manual | InTransit |
| InTransitToRepOrHosp | RFID | InTransit |
| LostInTransit | Manual | DC |
| LostInTransitOrAtRep | Timer | Unresolved |
| MfrDisposed | Manual | DC |
| MfrDisposedAssumed | RFID | DC |
| MfrDisposedRFID | RFID | DC |

TABLE 2-continued

| System dispositions, or state transitions | | |
|---|---|---|
| Disposition codes: | Type | DispositionGroup |
| NewProductAtDC | RFID | DC |
| Patient | Manual | Used |
| PendingHosp | Manual | PendingUsed |
| PendingMfr | Manual | PendingUsed |
| ReceivedByRep | Manual | InTransit |
| ReturnToMfr | RFID | Returned |
| ReturnToRep | Manual | Returned |
| UsedAtHosp | Timer | Used |
| UsedAtHospRFID | RFID | Used |
| UsedOrMovedHosp | RFID | PendingUsed |
| Wasted | Manual | Used |
| WrittenOffHosp | Manual | Used |
| WrittenOffMfr | Manual | Returned |

'ExpiredInHospital' is a disposition that is automated, based on date rather than an RFID read or lack thereof. No manual input can change this disposition; the product must be removed from the shelf to change its disposition. A product can expire at any location. Expired state is a function only of the expiration time, with the following exceptions: A product cannot expire after its final disposition, either not being present in any cabinet, or after being read by a trash reader.

An item moves to the 'LostInTransit' state based on time. If it has been InTransit for, typically, three days and has not been read by a cabinet, it is moved to 'LostInTransit' state. A timer is also used to move products to the 'GoneFromH' and 'GoneFromDC' states.

The detailed finite state machine implementation that is built into the application is based on the tables below. The numbers on each row corresponds to the numbers in the state diagrams of FIGS. 7-9. The states are based on: 1) the latest RFID read location of product, 2) whether it is read during the latest run, and 3) its current state.

The application determines: 1) the next state of the product item, and 2) the next disposition of the product item.

The last column in the tables below indicates the type of internal database action required to implement the state and disposition: 1) UpdateEvent: updates the last event's (disposition's) date and time; 2) InsertEvent: inserts a new event (disposition) in the database; and 3) SimulateEvent: inserts a new event and then processes the inserted state to insert another event.

SimulateEvent is done in error cases, where a product is at a DC or H, and then appears at the other type of entity (H or DC) without having departed its last location first. This type of read causes both a departure event from the last location and an arrival event at the new location to be written.

Table 3 shows the latest RFID read location, current read status and current state, and then the resulting next state and next disposition (state transition) for RFID reads that occur in a hospital RFID cabinet or at the DC as product is shipped or stored.

Table 4 shows the same information for RFID reads that occur in a hospital trash reader or DC trash reader.

TABLE 3

| States and transitions based on DC and hospital cabinet RFID reads | | | | | | |
|---|---|---|---|---|---|---|
| Cabinet/ Location | Read State | | Current State | Next State | Next Disposition | Action |
| DC | Read | 2 | None | ReadAtDC | NewProductAtDC | InsertEvent |
| | | 3 | ReadAtDC | NULL | NULL | UpdateEvent |
| | | 4 | NoLongerInDCCab | ReadAtDC | NewProductAtDC | InsertEvent* |
| | | 4a | ReadDCTrash | ReadAtDC | ErrorAtDCAfterGone | InsertEvent |
| | | 5 | GoneFromDC | ReadAtDC | ErrorAtDCAfterGone | InsertEvent |

TABLE 3-continued

States and transitions based on DC and hospital cabinet RFID reads

| Cabinet/Location | Read State | | Current State | Next State | Next Disposition | Action |
|---|---|---|---|---|---|---|
| | | 5a | GoneFromDCTrash | ReadAtDC | ErrorAtDCAfterGone | InsertEvent |
| | | 6 | ReadAtH | NoLongerInHCab | UsedOrMovedHosp | SimulateEvent |
| | | 7 | NoLongerInHCab | AtDCFromH | ReturnToMfr | InsertEvent |
| | | 7a | ReadHTrash | AtDCFromH | ReturnToMfr | InsertEvent |
| | | 8 | GoneFromH | AtDCFromH | ErrorAtDCAfterGone | InsertEvent |
| | | 8a | GoneFromHTrash | AtDCFromH | ErrorAtDCAfterGone | InsertEvent |
| | | 9 | AtDCFromH | NULL | NULL | UpdateEvent |
| | No | 10 | None | NULL | NULL | NULL |
| | Read | 11 | ReadAtDC | NoLongerInDCCab | InTransitToRepOrHosp | InsertEvent |
| | | 12 | NoLongerInDCCab | NULL | NULL | UpdateEvent |
| | | 12a | ReadDCTrash | NULL | NULL | UpdateEvent |
| | | 13 | GoneFromDC | NULL | NULL | NULL |
| | | 13a | GoneFromDCTrash | NULL | NULL | NULL |
| | | 14 | ReadAtH | NULL | NULL | NULL |
| | | 15 | NoLongerInHCab | NULL | NULL | NULL |
| | | 15a | ReadHTrash | NULL | NULL | NULL |
| | | 16 | GoneFromH | NULL | NULL | NULL |
| | | 16a | GoneFromHTrash | NULL | NULL | NULL |
| | | 17 | AtDCFromH | NoLongerInDCCab | MfrDisposedAssumed | InsertEvent |
| Hosp | Read | 18 | None | ReadAtH | ErrorRecdAtHosp | InsertEvent |
| | | 19 | ReadAtDC | NoLongerInDCCab | InTransitToRepOrHosp | SimulateEvent |
| | | 20 | NoLongerInDCCab | ReadAtH | InHospital | InsertEvent |
| | | 20a | ReadDCTrash | ReadAtH | ErrorAtHospAfterGone | InsertEvent |
| | | 21 | GoneFromDC | ReadAtH | ErrorAtHospAfterGone | InsertEvent |
| | | 21a | GoneFromDCTrash | ReadAtH | ErrorAtHospAfterGone | InsertEvent |
| | | 22 | ReadAtH | NULL | NULL | UpdateEvent |
| | | 23 | NoLongerInHCab | ReadAtH | InHospital | InsertEvent* |
| | | 23a | ReadHTrash | ReadAtH | ErrorAtHospAfterGone | InsertEvent |
| | | 24 | GoneFromH | ReadAtH | ErrorAtHospAfterGone | InsertEvent |
| | | 24a | GoneFromHTrash | ReadAtH | ErrorAtHospAfterGone | InsertEvent |
| | | 25 | AtDCFromH | ReadAtH | InHospital | SimulateEvent |
| | No | 26 | None | NULL | NULL | NULL |
| | Read | 27 | ReadAtDC | NULL | NULL | NULL |
| | | 28 | NoLongerInDCCab | NULL | NULL | NULL |
| | | 28a | ReadDCTrash | NULL | NULL | NULL |
| | | 29 | GoneFromDC | NULL | NULL | NULL |
| | | 29a | GoneFromDCTrash | NULL | NULL | NULL |
| | | 30 | ReadAtH | NoLongerInHCab | UsedOrMovedHosp | InsertEvent |
| | | 31 | NoLongerInHCab | NULL | NULL | UpdateEvent |
| | | 31a | ReadHTrash | NULL | NULL | UpdateEvent |
| | | 32 | GoneFromH | NULL | NULL | NULL |
| | | 32a | GoneFromHTrash | NULL | NULL | NULL |
| | | 33 | AtDCFromH | NULL | NULL | NULL |

*Unless, while product item is not in cabinet, a user enters a manual disposition for it. In that case, if the product item reappears on the hospital or DC shelf, its status is ErrorAtDCAAfterGone or ErrorAtHAfterGone.

TABLE 4

States and transitions based on DC and hospital trash reader RFID reads

| Cabinet/Location | Read State | | Current State | Next State | Next Disposition | Action |
|---|---|---|---|---|---|---|
| DC Trash | Read | 102 | None | ReadDCTrash | ErrorAtDCAfterGone | InsertEvent |
| | | 103 | ReadAtDC | ReadDCTrash | MfrDisposedRFID | UpdateEvent |
| | | 104 | NoLongerInfrDCCab | ReadDCTrash | MfrDisposedRFID | InsertEvent |
| | | 104a | ReadDCTrash | NULL | MfrDisposedRFID | UpdateEvent |
| | | 105 | GoneFromDC | ReadDCTrash | MfrDisposedRFID | InsertEvent |
| | | 105a | GoneFromDCTrash | ReadDCTrash | MfrDisposedRFID | InsertEvent** |
| | | 106 | ReadAtH | NoLongerInHCab | UsedOrMovedHosp | SimulateEvent |
| | | 107 | NoLongerInHCab | ReadDCTrash | MfrDisposedRFID | InsertEvent |
| | | 107a | ReadHTrash | ReadDCTrash | MfrDisposedRFID | InsertEvent |
| | | 108 | GoneFromH | ReadDCTrash | MfrDisposedRFID | InsertEvent |
| | | 108a | GoneFromHTrash | ReadDCTrash | MfrDisposedRFID | InsertEvent |
| | | 109 | AtDCFromH | ReadDCTrash | MfrDisposedRFID | UpdateEvent |
| | No | 110 | None | NULL | NULL | NULL |
| | Read | 111 | ReadAtDC | NULL | NULL | NULL |
| | | 112 | NoLongerInDCCab | NULL | NULL | NULL |
| | | 112a | ReadDCTrash | NULL | NULL | NULL |
| | | 113 | GoneFromDC | NULL | NULL | NULL |
| | | 113a | GoneFromDCTrash | NULL | NULL | NULL |
| | | 114 | ReadAtH | NULL | NULL | NULL |
| | | 115 | NoLongerInHCab | NULL | NULL | NULL |

TABLE 4-continued

States and transitions based on DC and hospital trash reader RFID reads

| Cabinet/Location | Read State | | Current State | Next State | Next Disposition | Action |
|---|---|---|---|---|---|---|
| | | 115a | ReadHTrash | NULL | NULL | NULL |
| | | 116 | GoneFromH | NULL | NULL | NULL |
| | | 116a | GoneFromHTrash | NULL | NULL | NULL |
| | | 117 | AtDCFromH | NULL | NULL | NULL |
| Hosp Trash | Read | 118 | None | ReadHTrash | ErrorAtHospAfterGone | InsertEvent |
| | | 119 | ReadAtDC | NoLongerInDCCab | InTransitToRepOrHosp | SimulateEvent |
| | | 120 | NoLongerInDCCab | ReadHTrash | UsedAtHospRFID | SimulateEvent |
| | | 120a | ReadDCTrash | ReadHTrash | ErrorAtHospAfterGone | InsertEvent |
| | | 121 | GoneFromDC | ReadHTrash | ErrorAtHospAfterGone | InsertEvent |
| | | 121a | GoneFromDCTrash | ReadHTrash | ErrorAtHospAfterGone | InsertEvent |
| | | 122 | ReadAtH | ReadHTrash | UsedAtHospRFID | InsertEvent |
| | | 123 | NoLongerInHCab | ReadHTrash | UsedAtHospRFID | InsertEvent |
| | | 123a | ReadHTrash | NULL | NULL | UpdateEvent |
| | | 124 | GoneFromH | ReadHTrash | UsedAtHospRFID | InsertEvent |
| | | 124a | GoneFromHTrash | ReadHTrash | UsedAtHospRFID | InsertEvent |
| | | 125 | AtDCFromH | ReadHTrash | InTransitToRepOrHosp | SimulateEvent |
| | No Read | 126 | None | NULL | NULL | NULL |
| | | 127 | ReadAtDC | NULL | NULL | NULL |
| | | 128 | NoLongerInDCCab | NULL | NULL | NULL |
| | | 128a | ReadDCTrash | NULL | NULL | NULL |
| | | 129 | GoneFromDC | NULL | NULL | NULL |
| | | 129a | GoneFromDCTrash | NULL | NULL | NULL |
| | | 130 | ReadAtH | NULL | NULL | NULL |
| | | 131 | NoLongerInHCab | NULL | NULL | NULL |
| | | 131a | ReadHTrash | NULL | NULL | NULL |
| | | 132 | GoneFromH | NULL | NULL | NULL |
| | | 132a | GoneFromHTrash | NULL | NULL | NULL |
| | | 133 | AtDCFromH | NULL | NULL | NULL |

**Items read when thrown in trash may be read again when trash is emptied. The timer filters out these reads.

The finite state machine also handles the 'NoInformation' and 'UnableToLocate' states and dispositions through associated logic; these are not driven by this table of logic. The 'NoInformation' state is used when a cabinet has been out of service for a predetermined period. The 'UnableToLocate' state is used when error conditions are inferred with the RFID tags on a medical item: when a tag has fallen off a product, has a duplicate serial number, or other problems.

The system manages the time differences in the clocks of the different cabinets, trash readers, application and database. It also handles cases where the cabinets are down and return to service with delayed reads, or network links are down between cabinets and the servers, delaying the transmission of their read data.

Manual State Transitions, or Dispositions

If the current state is 'NoLongerAtDC' or 'GoneFromDC', then Manual input can alter the default disposition from 'InTransitToRepOrHosp' or 'LostInTransitOrAtRep' to: 1) InTransitToRep: if known to be a rep PO; 2) InTransitToHosp: if known to be a hospital PO; 3) MfrDisposed: if known to be damaged or disposed at DC; 4) ReceivedByRep: if rep enters receipt in our system; 5) LostInTransit: if known to be lost from carrier report or other info; 6) PendingMfr or PendingHosp: known problem, still being investigated; 7) WrittenOffMfr or WrittenOffHosp: lost and not found, no longer being searched for; this is a terminal state for items that are never resolved.

If the current state is 'NoLongerInHospCab' or 'GoneFromH', Manual input can alter the default disposition from 'UsedOrMovedHosp' or 'UsedAtHosp' to: 1) Patient, if patient record number entered by hospital; 2) Defective, if 'did not cross' or other defect status entered by hospital; 3) Wasted, if entered by hospital; 4) ReturnToRep, if entered by rep or hospital; 5) InTransitToDC, if return entered by hospital; 6) PendingMfr or PendingHosp: known problem, still being investigated; 7) WrittenOffMfr or WrittenOffHosp: lost and not found, no longer being searched for; this is a terminal state for items that are never resolved.

If the current state is 'ReadHTrash' or 'GoneFromHTrash', the 'ReadHTrash' state, when available from RFID trash reads, supersedes the 'NoLongerInHCab' state and offers much greater certainty that the product was used. In practice, the hospital trash reader will result in substantially fewer unresolved dispositions, error dispositions and pending used dispositions, all of which are substantial problems operationally and occur frequently without a trash reader.

After a product item is read by the hospital trash reader, the following manual dispositions are allowed: 1) Patient, if patient record number entered by hospital; 2) Defective, if 'did not cross' or other defect status entered by hospital; 3) Wasted, if entered by hospital; 4) ReturnToRep, if entered by rep or hospital; 5) InTransitToDC, if return entered by hospital; 6) PendingMfr or PendingHosp: known problem, still being investigated; 7) WrittenOffMfr or WrittenOffHosp: lost and not found, no longer being searched for; this is a terminal state for items that are never resolved.

We allow these manual dispositions to be entered, even though we expect manual entry to happen much less frequently.

If the current state is 'ReadDCTrash' or 'GoneFromDCTrash', the 'ReadDCTrash' state when available from RFID trash reads, supersedes the 'NoLongerInDCCab' state and offers greater certainty that the product was disposed. In practice, the DC trash reader will result if substantially fewer unresolved dispositions and error dispositions, both of which are substantial problems operationally and occur frequently without a trash reader. After a product item is read by the DC trash reader, the following manual dispositions are allowed: 1) InTransitToRep: if known to be a rep PO; 2) InTransitToHosp: if known to be a hospital PO; 3) MfrDisposed: if known to be damaged or disposed at DC; 4) ReceivedByRep: if rep enters receipt in the system; 5) LostInTransit: if known to be lost from carrier report or other info; 6) PendingMfr or PendingHosp: known problem, still being investigated; 7) WrittenOffMfr or WrittenOffHosp: lost and not found, no longer being searched for; this is a terminal state for items that are never resolved The dispositions would almost never be entered, as they could occur only under quite unusual error conditions.

If the current state is 'NoInformation' because a cabinet or its network connection is offline, users can input the same manual dispositions as above. If necessary to continue tracking inventory via RFID, users should put product items in other operational cabinets. Users may not enter 'RFID' or 'Timer' dispositions if the current state is 'NoInformation'.

Figure 10:
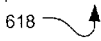
FIGS. 10 and 11 illustrate the user interface of the inventory tracking system of the present invention.
Figure 11:
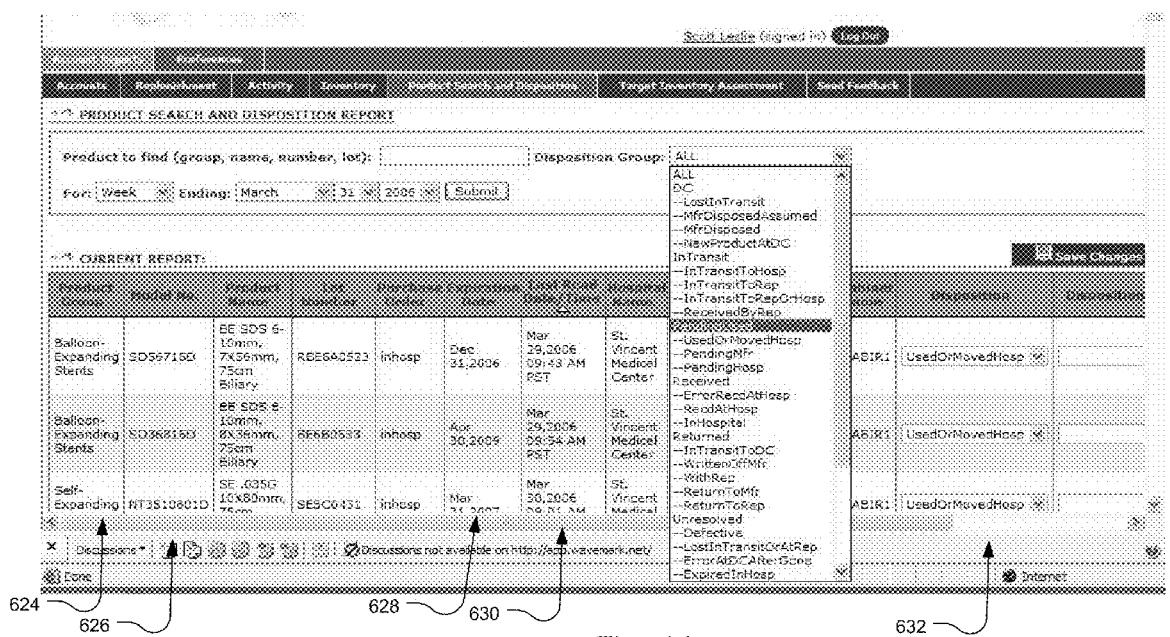

FIGS. 10 and 11 illustrate exemplary reports generated at the user interface 318 of the inventory management system 170.

Specifically, FIG. 10 illustrates an activity report. It provides information for various product groups, "blue stent," "green stent," . . . see 618. This provides information concerning those items that are used, pending, wasted. Also, there is a column 620 that is associated with stents within the group that have an unresolved status. It also shows other stents that have been returned and shipped in other columns. In this way, the user interface reports to the inventory personnel for the hospital information concerning use and inventory including unresolved medical items in the inventory.

FIG. 11 illustrates a product search and disposition report for the user interface 318. In this example, information associated with different "balloon-expanding stents" 624, with different model numbers 626, is presented, including expiration date 628 and date last read by and RFID reader is provided 630. It also enables manual changes to the disposition in column 632. The user is allowed to change the inventory status by modifying the pull-down menus contained in the disposition column. In this way, information for stents is manually modified to indicate other information that the inventory personnel have access to.

While this invention has been particularly shown and described with references to preferred embodiments thereof, it will be understood by those skilled in the art that various changes in form and details may be made therein without departing from the scope of the invention encompassed by the appended claims.

What is claimed is:

1. A refuse container system having a radio frequency identification (RFID) tag detection capability, the container system comprising:
    a container for holding refuse;
    a RFID antenna for reading RFID tags in the container; and
    an antenna conveyor for moving the RFID antenna relative to the container, the antenna conveyor extending vertically and longitudinally with respect to the container to transport the RFID antenna vertically and along a length of the container.

2. The system as claimed in claim 1, wherein the antenna conveyor comprises a lead screw.

3. The system as claimed in claim 1, further comprising:
    an inventory management system that receives and records RFID tag information detected by the RFID antenna; and
    an antenna conveyor controller for periodically controlling the antenna conveyor to move the RFID antenna relative to the container to collect RFID tag information for tags in the container.

4. The system as claimed in claim 1, further comprising a network interface for transmitting RFID tag information from the antenna onto a communications network.

5. The system as claimed in claim 1, further comprising an inventory management system that receives and records RFID tag information detected by the RFID antenna.

6. The system as claimed in claim 1, wherein the RFID antenna extends circumferentially around the container.

* * * * *